United States Patent [19]

Dorson, Jr. et al.

[11] 4,401,430
[45] Aug. 30, 1983

[54] METHOD OF AND APPARATUS FOR DETOXIFYING MAMMALIAN HOSTS

[75] Inventors: William J. Dorson, Jr.; Vincent B. Pizziconi, both of Tempe, Ariz.

[73] Assignee: Biomedical Labs., Tempe, Ariz.

[21] Appl. No.: 254,633

[22] Filed: Apr. 16, 1981

[51] Int. Cl.³ .............................................. A61M 1/03
[52] U.S. Cl. ...................................... 604/4; 424/230; 424/318; 424/303; 424/343; 604/49
[58] Field of Search ...................... 128/214 R, 213 R; 260/112 B; 424/101, 230, 318, 303, 343; 210/927; 604/4, 5, 6, 49

[56] References Cited

U.S. PATENT DOCUMENTS

| | | | |
|---|---|---|---|
| 3,697,645 | 10/1972 | Meier | 424/85 |
| 3,794,584 | 2/1974 | Kunin | 210/927 |
| 3,888,250 | 6/1975 | Hill | 128/214 R |
| 3,946,731 | 3/1976 | Lichtenstein | 128/214 R |
| 4,098,780 | 7/1978 | Lindroos | 260/112.5 R |
| 4,140,652 | 2/1979 | Korshak | 424/101 |
| 4,202,775 | 5/1980 | Abe | 210/927 |

FOREIGN PATENT DOCUMENTS 1562546  3/1980  United Kingdom ............ 128/214 R

OTHER PUBLICATIONS

R. Levine, Pharmacology-Drug Actions and Reactions.
A. Goldstein et al., Principles of Drug Action.

*Primary Examiner*—John C. Bleutge
*Assistant Examiner*—Patricia Short
*Attorney, Agent, or Firm*—Harry M. Weiss

[57] ABSTRACT

A method is described whereby a toxic or other unwanted substance which is bound to body protein in a host's plasma, cell membranes, or lipid materials such as adipose tissue, can be freed therefrom and rendered accessible for removal, modification or neutralization by engagement with a liberating agent, such as ethanol; and thereafter acting upon the freed substance to eliminate it from the host system or to neutralize or modify its effect within the system.

7 Claims, 2 Drawing Figures

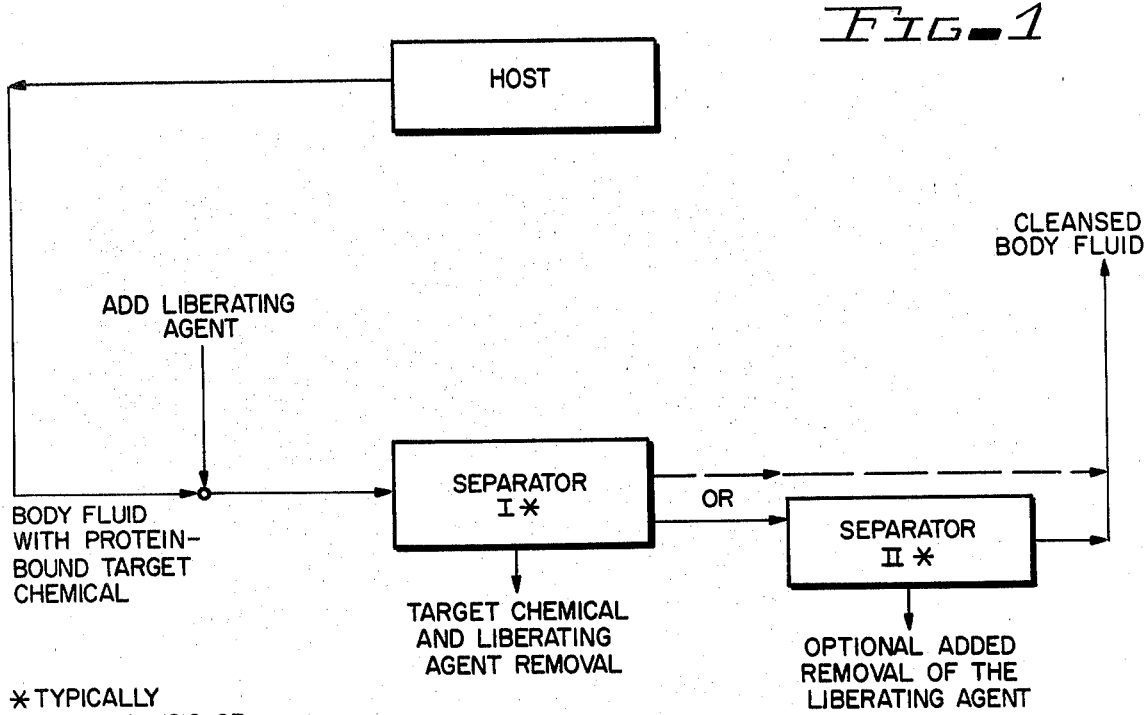
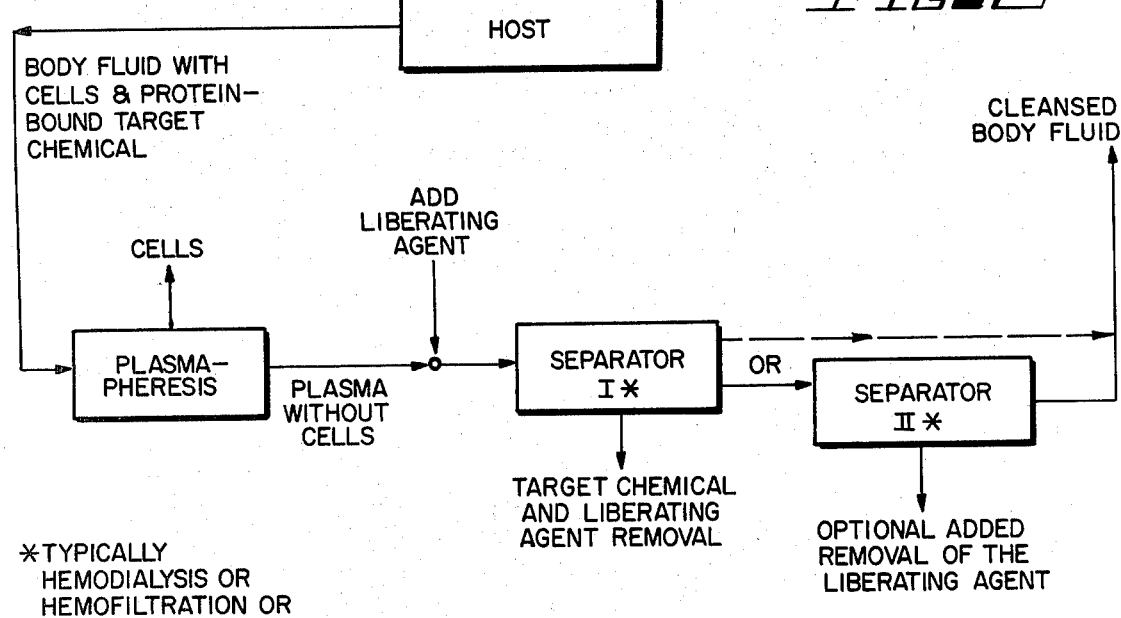

METHOD OF AND APPARATUS FOR DETOXIFYING MAMMALIAN HOSTS

INTRODUCTION

This invention relates to the negation of the effect of unwanted exogenous and endogenous substances which are bound to plasma proteins, cell membranes, or lipid materials such as adipose tissue in a mammalian host, especially those substances which are abused by the so-called drug culture such as narcotics, (e.g. morphine), barbiturates, tranquilizers, and hallucinogens, as well as selected trace elements, and metabolic intermediates such as bilirubin.

More particularly, the present invention provides a method whereby the aforesaid unwanted substances can be unbound and thus placed in condition for neutralization, modification, or removal by extracorporeal techniques of separation, such as hemofiltration, hemodialysis or hemoperfusion. The method, hereinafter described and illustrated, is based upon the discovery that the clearance efficiency of such substances can be enhanced by shifting from the bound to the unbound specie by adding a unique liberating agent such as ethanol, (ethyl alcohol) the effect of which is to unbind the specie from its protein base for removal in an extracorporeal apparatus such as a device for hemofiltration, hemoperfusion, or hemodialysis. The system may or may not contain an initial plasmapheresis step to separate cells from the body fluid prior to subsequent processing.

One important condition which the present invention is intended to resolve arises when a host overdoses on a dangerous substance with a known propensity for binding of the type represented by certain barbiturates, opiates and hypnotics and the like (so-called "downers") which, when taken in excess, place the host in a comatose condition, frequently on the verge of death.

The requirement for a quick, safe and efficient method of reducing the dangerous concentration from the host's blood stream is frequently essential if the host's life is to be saved.

The present invention meets this requirement by removing the protein-bound poison from the host, admixing the blood (or plasma) with a liberating agent to disengage the poison from the protein-moiety, separating the protein from the poison and the liberating agent, and returning the cleansed protein to the host where it is available to bind additional poison thereby reducing the concentration of free species from the host system and alleviating the adverse effects created by the higher free concentrations. This protein is then treated as before described to separate the poison therefrom and this procedure is repeated until the concentration of species in the host's system is reduced to a safe level and the host is removed from danger.

As will hereafter appear, the present invention is also useful to relieve patients who have overdosed on amphetamine and other so-called "uppers" which are likewise characterized by being bound to blood protein in the host system. In a similar manner, excessive concentrations of bilirubin, and other endogeneous toxins are effectively reduced by use of the present invention.

These and still further applications of this invention as will readily occur to the skilled artisan in light of the present disclosure, are based upon our discovery that a liberating agen, as hereinafter defined, will free a protein-bound substance from its protein base, that is, it will force a transition from the bound to the unbound state.

Thus, the present invention is predicated upon our discovery that highly beneficial effects are obtainable when a liberating agent, such as ethyl alcohol, engages a protein-bound substance to liberate a significant amount of the substance from its protein base and place it in condition for neutralization, modification, systemic dispersal or removal by the use of extracorporeal techniques such as hemoperfusion, hemofiltration, plasmapheresis or hemodialysis, depending upon the ultimate medical effect desired.

SUMMARY OF THE INVENTION

Accordingly, a prime object of the present invention is to provide a new and useful method and apparatus which is capable of achieving prompt and efficient release of a protein-bound substance from its protein base.

Still another object of the present invention is to provide a new and useful method whereby a systemic overdose of drug or like foreign substance can be quickly and efficiently reduced to a tolerable level.

A further object of the present invention is to provide a new and useful method and apparatus whereby an unwanted substance can be quickly and efficiently removed from the system of a poisoned host by conversion to a form readily entrapped with an extracorporeal device such as hemoperfusion, hemofiltration, plasmapheresis or hemodialysis.

A still further object of the present invention is to provide a novel and unique method whereby a preselected liberating agent is placed in position for strategic engagement with a protein-bound substance and is active to effect the separation of the protein from the substance.

These and still further objects as shall hereinafter appear are fulfilled by the present invention in a remarkably unexpected manner as will be readily discerned from a careful consideration of the following detailed description of exemplary embodiments thereof particularly when read in conjunction with the accompanying drawing in which:

BRIEF DESCRIPTION OF THE DRAWING

FIG. 1 is a schematic diagram of apparatus for practicing the present invention; and FIG. 2 is a schematic diagram of alternative apparatus for practicing the present invention.

DESCRIPTION OF THE PREFERRED EMBODIMENTS

In one practice of the present invention, the target chemical is admixed with a liberating agent. The target chemical may be an overdosed ingested drug which must be removed from the body, an intermediate biochemical which is present in aberrant amounts, or idiosyncratic toxins. The chemical is bound to blood protein, cell membrane, or lipid materials, like adipose tissue, and transported in the blood or other body fluid.

The liberating agent, defined below, frees the chemical of interest and increases its free soluble concentration relative to its bound concentration. By increasing the free soluble concentration of the chemical of interest, it is made accessible for removal, modification or reaction.

The term "liberating agent" as used herein defines a reagent which when added to a body fluid, increases the ratio of a free soluble chemical to the total content of that chemical in the body fluid. The total content is the aggregate of both the free soluble and bound states of the chemical. More than one physical mechanism can be encountered with the same resultant advantageous partitioning of the target chemical from the bound to the free soluble phase. Less than two percent by volume (% v/v) of ethanol has been found to be an effective liberating agent for protein bound drugs of abuse such as the barbiturates e.g. thiopental, secobarbital and pentobarbital and the tricyclics e.g. imipramine and chlorpromazine. Other liberating agents useful in the practice of this invention include lauric acid and sodium lauryl sulfonate which are effective for specific drugs such as thiopental; and acetylsalicylic acid which is specific for bilirubin. For most bound drugs of abuse, ethanol is effective and preferred over the other low carbon alcohols because of its lower toxicity. In general, liberating agents as herein defined are useful in body fluids and in vivo.

During the early phase of detoxification, it may not be desirable to return significant quantities of the liberating agent back to the mammal. If the target chemical separator does not adequately remove the liberating agent, a sequential removal device (hemoperfusion, hemodialysis, and hemofiltration types) can be placed either temporarily or permanently in the system. In one application, after the free soluble concentration of the target compound reaches safe levels in the body fluid, judicious introduction of the liberating agent can be desirable in transferring the body stores of the compound into the body fluid for continued efficient removal.

Concentration of ethanol in the range of 0.01% to about 2% v/v have been found satisfactory to accomplish the objectives stated herein in an extracorporeal circuit.

The present method can be practiced to achieve a nummber of beneficial medical and physiological effects. Thus, the liberation of an abused substance allows it to be quickly and readily removed from the patient's system by practicing the invention in an extracorporeal circuit, such as a hemoperfusion column, hemofiltration device, plasmapheresis unit, or hemodialysis device which is connected serially with the patient's blood system. When practicing the invention with substances for which the liberating agent, e.g. ethanol, is contraindicated it is important that an additional sorbent, such as activated charcoal, be placed in series to avoid infusion of the ethanol into the patient's system. When the concentration of free species in the patient's system is reduced to a tolerable level, physiologically acceptable liberating agents can be infused into the host system. The addition of the ethanol to the blood flow prior to its entry into the separator causes the bound agent to be freed and removed in the separator. The liberating agent can then be removed from the blood stream by either the same separator used for the target compound or by an additional specific device such as an activated charcoal column. The blood protein is returned to the patient's system whereupon the unoccupied protein sites are available to bind additional amounts of the chemical of interest, reducing the excessive concentration of free substance in the system. The process is repeated until the desired safe level of substance is achieved for the patient.

In another practice of the present invention, a physiologically acceptable liberating agent can be administered to the host, either per os or parenterally, and a sorbent, such as activated charcoal, ingested. As the liberating agent operates to partition the target chemical into the free state, it is removed by the sorbent. The sorbent with target chemical absorbed thereon, is thereafter eliminated by normal evacuation.

In another modification of the present invention, a physiologically acceptable liberating agent can be administered to the host, either per os or parenterally, and an extracorporeal separator system used to remove the target chemical from the host's blood stream.

Apparatus useful in the practice of the present invention include one or more extracorporeal separators such as a hemoperfusion device, a hemofiltration column, a membrane plasmapheresis device, and hemodialysis device arranged in the desired sequence to meet the exigencies of the specific treatment desired. In general, when the molecule to be collected has a molecular weight of 100 or less, hemodialysis is a separation of choice. When the molecules are larger, either hemoperfusion or hemofiltration will be the separation technique of choice. Membrane plasmapheresis has a special application to separate cells from plasma and may precede the addition of the liberating agent.

To further aid in the appreciation and comprehension of the present invention, and not to limit its scope, the following examples are presented.

EXAMPLE I

Thiopental was added to a human albumin solution at room temperature and allowed to equilibrate. Relative absorbances, proportional to free drug concentration, were measured spectrophotometrically (uv). An ethanol concentration of 0.1% v/v resulted in an increase in relative absorbance equivalent to a 30 to 70% increase in free drug concentration in the pH range of 5.6 to 9.2.

EXAMPLE II

Thiopental was added to fresh human plasma at room temperature and allowed to equilibrate. Thin layer chromatography, used as an indicator of free drug concentration, was compared to thiopental calibrated plates. Ethanol concentrations of 0, 0.1, 0.2, 0.3, 0.4, 0.5, 0.6, 0.7, 0.8 and 1.0% v/v were tested. A maximum free drug concentration occurred at and above 0.6% v/v.

EXAMPLE III

Thiopental was added to fresh human plasma at room temperature and allowed to equilibrate. Relative absorbances, proportional to free drug concentration, were measured spectrophotometrically (uv). Ethanol concentrations of 0, 0.4, 0.7, 1.0, and 1.4% v/v were tested. Drug/plasma and drug/plasma/ethanol solutions were equilibrated with coated activated charcoal. A 13% change in relative absorbance from 0 to 1.4% v/v ethanol indicated significant increased adsorption of the drug by charcoal.

EXAMPLE IV

Pentobarbital was added to a human albumin solution at room temperature and allowed to equilibrate. Differential solution pH changes, related to free drug concentration, were measured. Ethanol concentrations of 0, 0.2, 0.4, 0.6, 0.8 and 1.0% v/v were tested and showed a maximum differential pH change (maximum free soluble drug concentration) at 0.6% v/v ethanol.

EXAMPLE V

Thiopental was added to a human albumin solution at room temperature and allowed to equilibrate. Differential solution pH changes, related to free drug concentration, were measured. Concentrations of 0, 2, 4, 6, 8, and 10 mg/ml of sodium lauryl sulfate resulted in a continuous pH change which demonstrated increasing free soluble drug concentrations.

EXAMPLE VI

Chlorpromazine HCl, a tranquilizer, was added to a human albumin solution at room temperature and allowed to equilibrate. Differential solution pH changes, related to free drug concentration, were measured. Ethanol concentrations of 0, 0.2, 0.4, 0.6, 0.8 and 1.0% v/v resulted in continuous pH changes which demonstrated increases in free soluble concentration of this drug.

EXAMPLE VII

Imipramine HCl, an antidepressant, was added to a human albumin solution at room temperature and allowed to equilibrate. Differential solution pH changes, related to free drug concentration, were measured. Ethanol concentrations of 0, 0.2, 0.4, 0.6, 0.8 and 1.0% v/v were tested. Differential pH responses at 0.2, 0.4% v/v and above demonstrated significant increases in the free soluble drug concentration.

EXAMPLE VIII

Tricyclic antidepressants are a common class of drugs of abuse which are present in an emergency medical situation. As an example, the highly bound drug imipramine of Example VII may be removed by the extracorporeal means of this invention. Blood from the typically comatose patient may be directed, by cannulation, to an admixture joint where an osmotically balanced ethanol solution is added in proportion to the controlled blood flow rate, usually by a pump. The blood mixture is then passed into either a hemoperfusion column, normally containing coated activated charcoal, or a membrane based hemofiltration device, whichever is preferred. Hemoperfusion, if available, is preferred to hemofiltration because of its improved efficiency. The coated activated charcoal will remove both the imipramine and ethanol effectively and efficiently. The column must be replaced before either the free soluble imipramine or the ethanol reach appreciable concentrations at the column exit. When the patient's blood concentration reaches a safe level, some ethanol may be administered to the patient to expedite release of the drug from the body stores into the blood stream for treatment in the manner described.

From the foregoing, it becomes apparent that new and quite remarkable methods and apparatus have been herein described and illustrated which have the surprising ability when used in conjunction with a host to reduce the concentration of unwanted substances. The above description of preferred embodiments is given by way of example only. Changes in form and details may be made therein by one skilled in the art without departing from the scope of the invention as defined by the appended claims. For example, the method and apparatus of this invention is particularly amenable to operation on protein-bound substances; however, the method and apparatus of this invention may likewise be amenable to substances bound to other biochemicals (other than protein) such as carbohydrates, fats, and combinations thereof or with proteins.

What is claimed is:

1. In detoxifying a mammalian host, the method which comprises extra-corporeal treatment of biological fluid derived from said host and containing protein-bound toxicant, with a physiologically acceptable chemical agent capable of liberating the toxicant from the protein without replacing the toxicant at the protein moiety and without adversely affecting the fluid at the concentration employed by increasing the ratio of said toxicant's free soluble form to the total content of said toxicant.

2. A method according to claim 1 in which the treated fluid is returned to said host.

3. A method according to claim 1 in which said toxicant is selected from the group consisting of those drugs of abuse having the propensity to bind onto protein.

4. A method according to claim 1 in which said liberating agent is selected from the group consisting of sodium lauryl sulfonate, lauric acid, acetylsalicylic acid, and lower carbon alcohols.

5. A method according to claim 1, in which said toxicant is selected from the group consisting of tricyclics and barbiturates and said liberating agent is ethanol.

6. A method according to claim 1 in which said protein-bound toxicant is transported in a biological fluid and said fluid is separated into plasma and cellular portions prior to engagement with said liberating agent.

7. In detoxifying a mammalian host, the method which comprises extra-corporeal treatment of biological fluid derived from said host and containing biochemical—bound toxicant, with a physiologically acceptable agent capable of liberating the toxicant from the biochemical without replacing the toxicant at the chemical moiety and without adversely affecting the fluid at the concentration employed, by increasing the ratio of said toxicant's free soluble form to the total content of said toxicant.

* * * * *